(12) United States Patent
Ingleson et al.

(10) Patent No.: US 8,130,377 B2
(45) Date of Patent: Mar. 6, 2012

(54) SPECTROPHOTOMETER SYSTEM WITH MODULAR 45/0 HEAD

(75) Inventors: Alan Ingleson, Newbury (GB); Joseph Reed, Carversville, PA (US)

(73) Assignee: Datacolor Holding AG, Lucerne (CH)

( * ) Notice: Subject to any disclaimer, the term of this patent is extended or adjusted under 35 U.S.C. 154(b) by 422 days.

(21) Appl. No.: 12/486,334

(22) Filed: Jun. 17, 2009

(65) Prior Publication Data
US 2009/0316149 A1 Dec. 24, 2009

Related U.S. Application Data

(60) Provisional application No. 61/074,021, filed on Jun. 19, 2008.

(51) Int. Cl.
G01J 3/40 (2006.01)
(52) U.S. Cl. ........................ 356/302; 356/319
(58) Field of Classification Search .................. 356/300, 356/302, 319, 320, 402
See application file for complete search history.

(56) References Cited

U.S. PATENT DOCUMENTS

| 4,995,727 | A | * | 2/1991 | Kawagoe et al. | ............ 356/402 |
|---|---|---|---|---|---|
| 5,377,000 | A | | 12/1994 | Berends | |
| 5,923,039 | A | | 7/1999 | Jablonski et al. | |
| 6,147,761 | A | | 11/2000 | Walowit et al. | |
| 6,631,000 | B1 | * | 10/2003 | Schwarz | ........................ 356/445 |
| 6,844,931 | B2 | | 1/2005 | Ehbets | |
| 7,369,244 | B2 | * | 5/2008 | Imura | ........................... 356/446 |
| 7,872,753 | B2 | * | 1/2011 | Frankinet | ...................... 356/445 |
| 2006/0203240 | A1 | | 9/2006 | Ingleson | |

OTHER PUBLICATIONS

International Search Report and Written Opinion for PCT/US2009/047657, Aug. 12, 2009, copy consists of 10 pages.

* cited by examiner

Primary Examiner — Roy M Punnoose

(57) ABSTRACT

In one embodiment, the invention is a spectrophotometer with a modular 45/0 head. One embodiment of an apparatus for measuring a reflectance of a sample includes a plurality of light emitting diodes for emitting light, a reflective housing positioned above the plurality of light emitting diodes, where the reflective housing is a dome having a plurality of apertures formed around its perimeter, a sample channel for capturing a first portion of the light, where the first portion of the light interacts with the sample, and a reference channel for capturing a second portion of the light, where the second portion of the light is independent of the sample.

20 Claims, 4 Drawing Sheets

| X | Y |
|---|---|
| 0 | 0.193 |
| 0.25 | 0.3756 |
| 0.5 | 0.5484 |
| 0.75 | 0.7129 |
| 1 | 0.8701 |
| 1.25 | 1.0202 |
| 1.5 | 1.1639 |
| 1.75 | 1.302 |
| 2 | 1.4348 |
| 2.25 | 1.5628 |
| 2.5 | 1.6861 |
| 2.75 | 1.8051 |
| 3 | 1.9201 |
| 3.25 | 2.0313 |
| 3.5 | 2.1388 |
| 3.75 | 2.243 |
| 4 | 2.3439 |
| 4.25 | 2.4418 |
| 4.5 | 2.5366 |
| 4.75 | 2.6291 |
| 5 | 2.7181 |
| 5.25 | 2.8048 |
| 5.5 | 2.8891 |
| 5.75 | 2.9709 |
| 6 | 3.0502 |
| 6.25 | 3.1275 |
| 6.5 | 3.2027 |
| 6.75 | 3.2756 |
| 7 | 3.3466 |
| 7.25 | 3.4155 |
| 7.5 | 3.4824 |
| 7.75 | 3.5475 |
| 8 | 3.6108 |
| 8.25 | 3.6723 |
| 8.5 | 3.7321 |

FIG. 3

SPECTROPHOTOMETER SYSTEM WITH MODULAR 45/0 HEAD

CROSS REFERENCE TO RELATED APPLICATIONS

This application claims the benefit of U.S. Provisional Patent Application No. 61/074,021, filed Jun. 19, 2008, which is herein incorporated by reference in its entirety.

FIELD OF THE INVENTION

The present invention generally relates to the field of reflectance measurement, and more specifically relates to portable spectrophotometers.

SUMMARY OF THE INVENTION

In one embodiment, the invention is a spectrophotometer with a modular 45/0 head. One embodiment of an apparatus for measuring a reflectance of a sample includes a plurality of light emitting diodes for emitting light, a reflective housing positioned above the plurality of light emitting diodes, where the reflective housing is a dome having a plurality of apertures formed around its perimeter, a sample channel for capturing a first portion of the light, where the first portion of the light interacts with the sample, and a reference channel for capturing a second portion of the light, where the second portion of the light is independent of the sample.

BRIEF DESCRIPTION OF THE DRAWINGS

The teachings of the present invention can be readily understood by considering the following detailed description in conjunction with the accompanying drawings, in which:

FIG. 3 is a table illustrating measured results for the exemplary shape of the reflective housing.

DETAILED DESCRIPTION

In one embodiment, the invention is a spectrophotometer with a modular 45/0 head. The spectrophotometer has a relatively compact, lightweight size and is relatively easy to assemble due to its modular nature.

Figure 1:
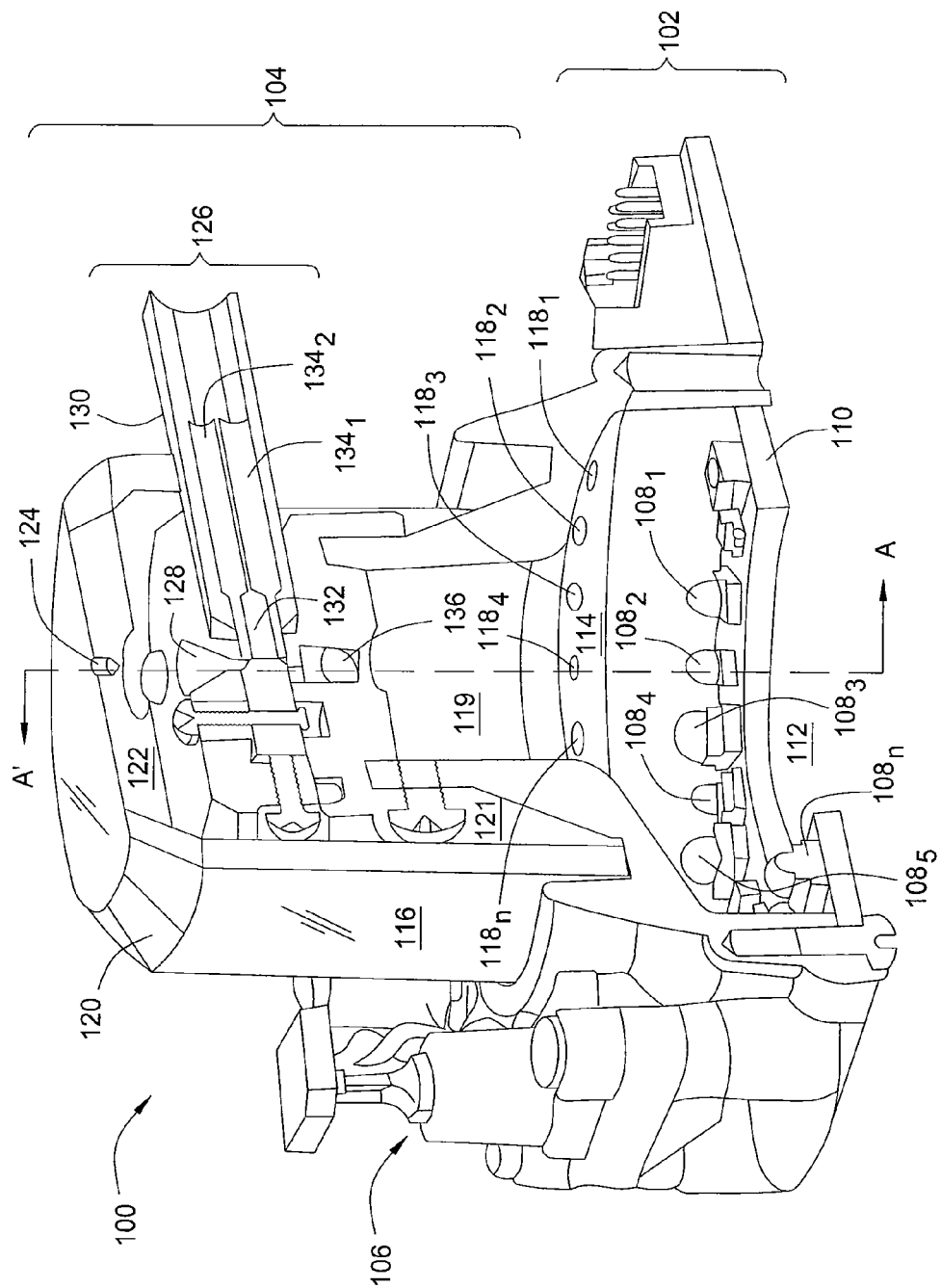
FIG. 1 is a two-dimensional side sectional view of one embodiment of a spectrophotometer, according to the present invention.

FIG. 1 is a two-dimensional side sectional view of one embodiment of a spectrophotometer 100, according to the present invention. The spectrophotometer is configured to measure the reflectance of a sample. The spectrophotometer 100 is substantially symmetrical about a central vertical axis A-A'. As illustrated, the spectrophotometer 100 comprises a light source 102 and a chamber 104 coupled to the light source 102. In a further embodiment, the spectrophotometer also includes a gloss detector 106 coupled to the light source 102. The gloss detector 106 is configured to measure the ability of the sample to reflect light into the specular direction.

The light source 102 comprises a plurality of light emitting diodes (LEDS) $108_1$-$108_n$ (hereinafter collectively referred to as "LEDs 108") arranged around the perimeter of a ring-shaped base 110. The center of the ring-shaped base 110 comprises a sample port 112 near which a sample whose reflectance is to be measured is placed. In one embodiment, the plurality of light emitting diodes 108 includes light emitting diodes of at least two spectral types. In one embodiment, the light source 102 comprises twenty-seven LEDs 108: three each of nine spectral types of LEDs (e.g., warm-white LED with a blue phosphor, etc.). In this embodiment, the three LEDs for each spectral type are positioned at intervals of approximately 120 degrees around the ring-shaped base 110 (i.e., such that each of the three LEDs is separated from the next by approximately 120 degrees). Collectively, the LEDs 108 emit substantially the full spectrum of visible light and are able to provide power at substantially all visible wavelengths. In an alternative embodiment, one or more LEDs that can individually emit substantially the full spectrum of visible light are used in place of multiple different spectral types of LEDs. In one embodiment, each LED 108 includes a lens (not shown).

The chamber 104 comprises at least two major parts: a reflective housing 114 and a transparent light guide 116. The reflective housing 114 is positioned directly above the light source 102 and comprises a dome formed of metal or metalized plastic. At least the interior surface of the reflective housing 114 (i.e., the surface that faces the light source 102) is reflective. The reflective housing 114 further comprises a plurality of apertures $118_1$-$118_n$ (hereinafter collectively referred to as "apertures 118"). Each of the apertures 118 is positioned directly above one of the LEDs 108 of the light source 102. In addition, the reflective housing comprises one large aperture formed substantially in the center of the dome, such that a first hollow chamber 119 is created in the center of the spectrophotometer 100.

The transparent light guide 116 is positioned directly above the reflective housing 114 and comprises a cylinder formed of an optical-grade transparent material that is capable of acting as a light guide (e.g., acrylic). A faceted mirror 120 is positioned in a ring around the interior perimeter of the cylinder's ceiling 122. In addition, a conical-shaped indentation 124 is positioned in approximately the center of the ceiling. A space created between the transparent light guide 116 and the reflective housing 114 serves as a second hollow chamber 121.

In addition, the transparent light guide 116 houses a fiber optic assembly 126. The fiber optic assembly 126 comprises a mirror 128 and a fiber optic ferrule 130. The mirror 128 is positioned directly below the deformation 124 in the cylinder's ceiling 122. In one embodiment, the mirror 128 is angled at approximately forty-five degrees relative to the spectrophotometer's central vertical axis A-A'. The fiber optic ferrule 130 comprises an input 132 positioned proximate to the mirror 128 and extends outward therefrom (i.e., toward an exterior of the spectrophotometer) in an orientation substantially perpendicular to the spectrophotometer's central vertical axis A-A'. The fiber optic ferrule 130 comprises at least a first optical fiber $134_1$ and a second optical fiber $134_2$ (hereinafter collectively referred to as "optical fibers 134"). The first optical fiber $134_1$ and a second optical fiber $134_2$ are substantially parallel to each other. In addition, the fiber optic assembly 126 comprises an achromatic lens 136 positioned between the fiber optic ferrule 130 and the reflective housing 114.

In operation, the sample whose reflectance is to be measured is placed near the sample port 112, and the LEDs 108 are activated to illuminate the sample. A first portion of the light that is emitted by the LEDs 108 passes through the apertures 118 in the reflective housing 114 and vertically upward through the transparent light guide 116, within the second hollow chamber 121. When the light reaches the faceted mirror 120, the light is reflected toward the conical indentation 124 in the cylinder's ceiling 122, which in turn reflects the light vertically downward toward mirror 128. The angle of the mirror 128 directs the light through the input 132 of the fiber optic ferrule 130. The light is then output over the first optical fiber $134_1$ as a reference channel. This reference-channel light may be output, for example, to a light-measuring device that is external to the spectrophotometer 100. The term "reference channel" is used interchangeably herein to refer to both the light that is independent of (does not interact with) the sample and to the mechanisms for producing the reference channel light.

A second portion of the light that is emitted by the LEDs 108 is reflected by the interior surface of the reflective housing 114 and is incident on the sample. In one embodiment, the reflective housing is configured to converge the otherwise diverging beams of light emitted by the LEDs 108 and to reflect the light so that it is incident on the sample at an angle of approximately forty-five degrees. In one embodiment, this beam divergence is further minimized by the lens (discussed above) that is included in each LED 108. The light is reflected by the sample and passes through the first hollow chamber 119 and the achromatic lens 136, which, with the aid of the angled mirror 128, focuses the collimated light through the input 132 onto the fiber optic ferrule 130. The light is then output over the second optical fiber $134_2$ as a sample channel. This sample-channel light may be output, for example, to a light-measuring device that is external to the spectrophotometer 100. The term "sample channel" is used interchangeably herein to refer to both the light that is interacts with the sample and to the mechanisms for producing the sample channel light.

The generation of both reference-channel light and sample-channel light enables the reflectance of the sample to be measured accurately. Specifically, light from same light source (i.e., the LEDs 108) can be compared as captured through the reference channel (which is independent of the sample) and as captured through the sample channel (through which the light interacts with the sample).

The spectrophotometer 100 maintains a modular structure, which allows for ease of manufacture. In particular, the configuration of the fiber optic assembly 126 enables precise sub-assembly of its components prior to assembly of the spectrophotometer 100. The spectrophotometer also maintains a relatively compact and lightweight size, which allows for easily portability.

Figure 2:
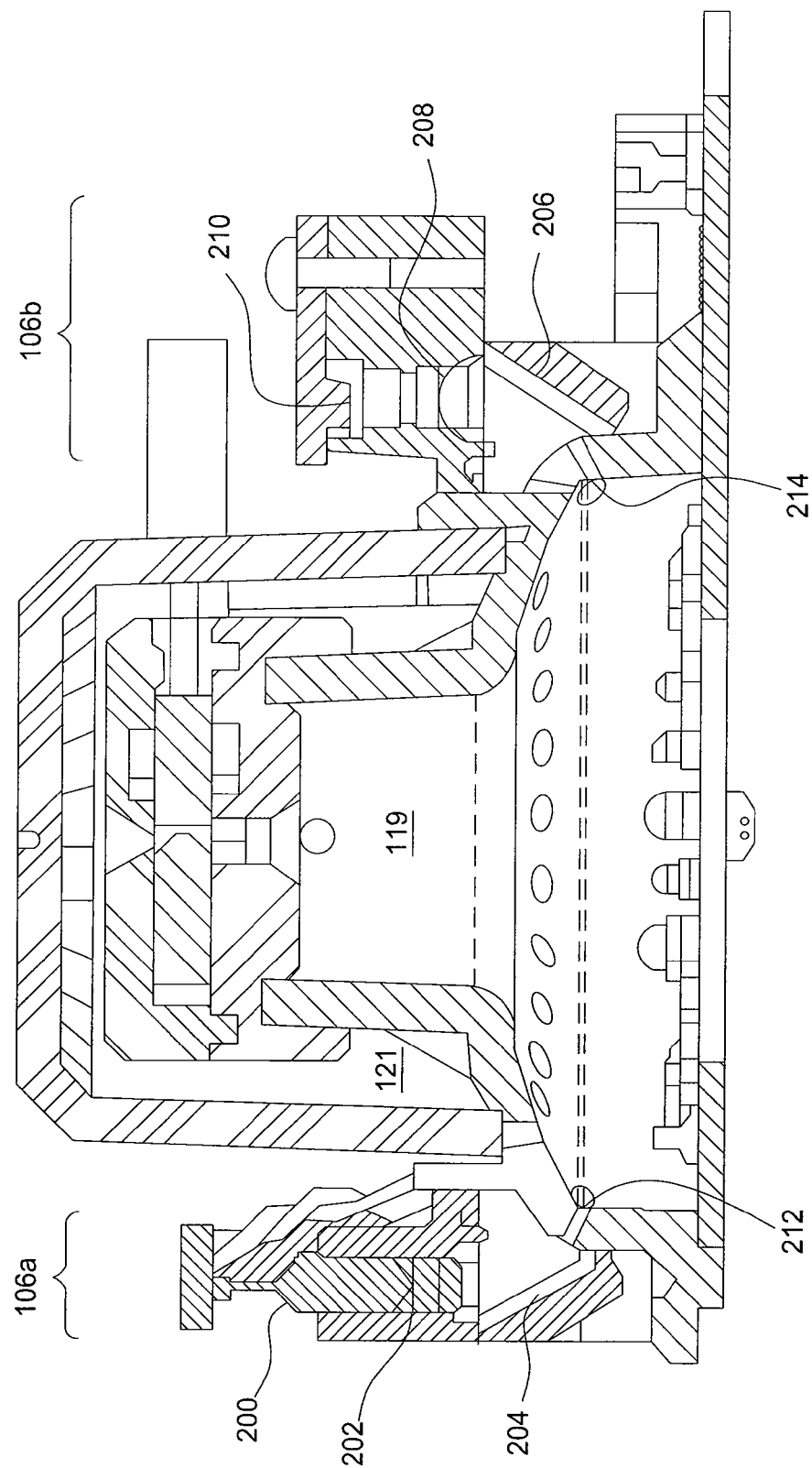
FIG. 2 is another two-dimensional side sectional view of the spectrophotometer of FIG. 1, in which the gloss detector is fully illustrated.

FIG. 2 is another two-dimensional side sectional view of the spectrophotometer 100 of FIG. 1, in which the gloss detector 106 is fully illustrated. As illustrated, the gloss detector 106 is coupled laterally from the reflective housing 114.

As illustrated, the gloss detector 106 comprises a first section 106a coupled to one side of the reflective housing 114 and a second section 106b coupled to an opposite side of the reflective housing 114. The first section 106a comprises an emitter LED 200 positioned vertically above a first achromatic lens 202. A first mirror 204 is positioned vertically below the first achromatic lens 202. In one embodiment, the first mirror 204 is angled at approximately sixty degrees relative to the central vertical axis A-A' of the spectrophotometer 100.

The second section 106b comprises a light-to-frequency converter 210 positioned vertically above a second achromatic lens 208. A second mirror 206 is positioned vertically below the second achromatic lens 208. In one embodiment, the second mirror 206 is angled at approximately sixty degrees relative to the central vertical axis A-A' of the spectrophotometer 100.

In operation, the emitter LED 200 emits a beam of light that is directed through the first achromatic lens 202. The LEDs 108 contained in the light source 102 are not illuminated at this time. The first achromatic lens 202 directs the light to the first mirror 204, which reflects and re-directs the light through a first gloss meter aperture 212 in the side of the reflective housing 114. The first gloss meter aperture 212 is different from the apertures 118 that are discussed above with respect to FIG. 1.

The light that is directed through the first gloss meter aperture 212 impinges on the sample. The light reflected by the sample exits through a second gloss meter aperture 214 in the side of the reflective housing 114. Light that exits through the second gloss meter aperture 214 is reflected and redirected by the second mirror 206, which directs the light through the second achromatic lens 208. Light directed through the second achromatic lens 208 is captured by the light-to-frequency converter 210. The light-to-frequency converter 210 converts the captured light to a pulse train whose frequency is directly proportional to the intensity of the captured light.

The angled first and second mirrors 204 and 206 therefore fold the path of the light as it is emitted by the emitter LED 200, reflected by the sample, and captured by the light-to-frequency converter 210. Folding of the path allows the spectrophotometer 100 to maintain a relatively compact and modular size.

One embodiment of a quantitative prescription is provided below for the shape of the interior surface of the reflective housing 114. In one embodiment, the reflective housing 114 is shaped so as to deflect the light emitted by the LEDs 108 onto the sample at an angle of approximately forty-five degrees. This shape is based on an embodiment obtained by iterated simulation in a computer-aided-design ray-trace program.

In this simulation, the exemplary shape of the reflective housing 114 (which in one embodiment is embodied in thirty-five points) was digitized and fit by a sixth-degree polynomial. This gave results within a digitization accuracy (±0.2 um, i.e., ±200 nm). The regression polynomial appears in EQN. 1 below (wherein the horizontal coordinate X and vertical coordinate Y are in millimeters):

$$Y=-0.000002566412*X^6+0.00008590337*X^5-0.001241492*X^4+0.010865*X^3-0.08105109*X^2+0.7481436*X+0.1932124 \quad \text{(EQN. 1)}$$

FIG. 3 is a table illustrating measured results for the exemplary shape of the reflective housing 114 (i.e., the thirty-five points referenced above), based on the use of EQN. 1. In accordance with these results, (X, Y)=(0, 0) is the position of the left hand bottom part of the reflective housing 114.

Figure 4:
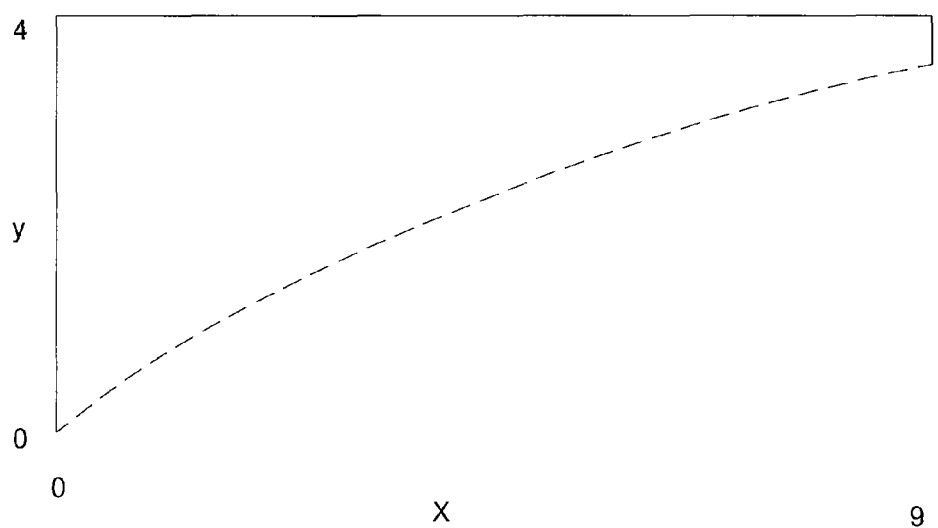
FIG. 4 is a plot illustrating the shape of the reflective housing in radial section, where X and Y are in millimeters.

FIG. 4 is a plot illustrating the shape of the reflective housing 114 in radial section, where X and Y are in millimeters. To obtain the three-dimensional shape, the plot is rotated about a center axis at the right.

While the foregoing is directed to embodiments of the present invention, other and further embodiments of the invention may be devised without departing from the basic scope thereof. Various embodiments presented herein, or portions thereof, may be combined to create further embodiments. Furthermore, terms such as top, side, bottom, front, back, and the like are relative or positional terms and are used with respect to the exemplary embodiments illustrated in the figures, and as such these terms may be interchangeable.

What is claimed is:

1. An apparatus for measuring a reflectance of a sample positioned at a sample port, comprising:
   a plurality of light emitting diodes for emitting light;
   a reflective housing positioned above the plurality of light emitting diodes, the reflective housing comprising a dome having a plurality of apertures formed around a perimeter of the dome for passing the light therethrough;
   a sample channel for guiding a first portion of the light, where the first portion of the light interacts with the sample; and
   a reference channel for guiding a second portion of the light, where the second portion of the light is independent of the sample.

2. The apparatus of claim 1, wherein the plurality of light emitting diodes is arranged around a perimeter of a ring-shaped base.

3. The apparatus of claim 2, wherein the sample port is positioned in a center of the ring-shaped base.

4. The apparatus of claim 2, wherein the plurality of light emitting diodes comprises light-emitting diodes of at least two different spectral types.

5. The apparatus of claim 1, wherein the plurality of light emitting diodes collectively emits substantially a full spectrum of visible light.

6. The apparatus of claim 1, wherein the reflective housing is shaped to reflect the first portion of the light toward the sample port.

7. The apparatus of claim 6, wherein the reflective housing is shaped to reflect the first portion of the light such that the first portion of the light is incident upon the sample port at an angle of approximately forty-five degrees relative to a central vertical axis of the apparatus.

8. The apparatus of claim 6, wherein the dome has a reflective interior surface that faces the plurality of light emitting diodes.

9. The apparatus of claim 6, further comprising:
   a lens positioned to receive the first portion of the light from the reflective housing; and
   a mirror positioned to direct the first portion of the light from the lens to an optical fiber, wherein the optical fiber is configured to carry the first portion of the light out of the apparatus.

10. The apparatus of claim 1, wherein each of the plurality of apertures is positioned directly above one of the plurality of light emitting diodes.

11. The apparatus of claim 1, wherein the reference channel comprises a light guide coupled to the reflective housing, the light guide comprising:
    a cylindrical body extending vertically from the reflective housing, the cylindrical body being shaped to guide the second portion of the light;
    a faceted mirror formed around a perimeter of a ceiling of the cylindrical body, the faceted mirror being shaped to reflect the second portion of the light that is guided by the cylindrical body in a first direction;
    an indentation formed in the ceiling of the cylindrical body, the indentation being shaped to receive the second portion of the light reflected by the faceted mirror and to reflect the second portion of the light in a second direction; and
    a mirror positioned to direct the second portion of the light from the indentation to an optical fiber, wherein the optical fiber is configured to carry the second portion of the light out of the apparatus.

12. The apparatus of claim 1, further comprising a gloss detector coupled to the sample channel.

13. The apparatus of claim 12, wherein the gloss detector comprises:
    an emitter light emitting diode positioned outside of the sample channel;
    a first set of optics for directing a beam of light emitted by the emitter light emitting diode through a portion of the apparatus;
    a second set of optics for capturing at least a portion of the beam of light from the portion of the apparatus; and
    a light-to-frequency converter positioned to receive the at least a portion of the beam of light from the second set of optics.

14. The apparatus of claim 13, wherein the first set of optics comprises:
    a mirror positioned to direct the beam of light from the emitter light emitting diode to the portion of the apparatus; and
    an aperture formed in the apparatus and positioned to receive the beam of light from the mirror.

15. The apparatus of claim 14, wherein the mirror is oriented at an angle of approximately sixty degrees relative to a central vertical axis of the apparatus.

16. The apparatus of claim 13, wherein the second set of optics comprises:
    an aperture formed in the apparatus and positioned to receive the at least a portion of the beam of light; and
    a mirror positioned to receive the at least a portion of the beam of light and to direct the at least a portion of the beam of light toward the light-to-frequency converter.

17. The apparatus of claim 16, wherein the mirror is oriented at an angle of approximately sixty degrees relative to a central vertical axis of the apparatus.

18. An apparatus for measuring a reflectance of a sample positioned at a sample port, comprising:
    a ring-shaped base having the sample port formed in a center thereof;
    a plurality of light-emitting diodes arranged around a perimeter of the ring-shaped base;
    a reflective dome positioned above the plurality of light-emitting diodes, wherein the reflective dome comprises a reflective interior surface and a plurality of apertures formed around a perimeter thereof, each of the plurality of apertures being positioned directly above one of the plurality of light emitting diodes;
    a light guide coupled to the reflective dome and extending upward therefrom, wherein the light guide comprises a cylindrical body, a faceted mirror formed around a perimeter of a ceiling of the cylindrical body, and an indentation formed in a center of the ceiling; and
    a fiber optic assembly coupled to the reflective dome and to the light guide, the fiber optic assembly comprising at least two optical fibers.

19. The apparatus of claim 18, further comprising a gloss detector coupled to the reflective dome, the gloss detector comprising:
    an emitter light emitting diode coupled to a first side of the reflective dome; and
    a light-to-frequency converter coupled to a second side of the reflective dome, wherein the second side of the reflective dome is positioned opposite from the first side of the dome.

20. The apparatus of claim 18, wherein the plurality of light emitting diodes comprises light-emitting diodes of at least two different spectral types.

* * * * *